United States Patent [19]

Cobb

[11] Patent Number: 4,596,896

[45] Date of Patent: Jun. 24, 1986

[54] ACID CATALYZED REACTIONS OF MONOVINYL AROMATIC COMPOUNDS

[75] Inventor: Raymond L. Cobb, Bartlesville, Okla.

[73] Assignee: Phillips Petroleum Company, Bartlesville, Okla.

[21] Appl. No.: 740,781

[22] Filed: Jun. 3, 1985

[51] Int. Cl.$^4$ .............................. C07C 2/04; C07C 2/42
[52] U.S. Cl. ..................................... 585/320; 568/631;
568/633; 570/129; 570/181; 585/323; 585/425;
585/428; 585/436
[58] Field of Search ............... 585/320, 323, 425, 428,
585/375, 376, 436; 568/631, 633; 570/129, 184

[56] References Cited

U.S. PATENT DOCUMENTS

| | | | |
|---|---|---|---|
| 2,429,719 | 10/1947 | Hersberger et al. | 585/428 |
| 2,646,450 | 7/1953 | Thuber | 585/406 |
| 2,851,501 | 9/1958 | Benz et al. | 585/410 |
| 3,305,905 | 5/1968 | Smith et al. | 585/406 |
| 3,686,339 | 8/1972 | Schecker et al. | 585/406 |
| 3,769,359 | 10/1973 | Massie | 585/428 |
| 3,849,507 | 11/1974 | Zuech | 585/468 |
| 3,985,818 | 10/1976 | Numata et al. | 585/406 |
| 4,254,292 | 3/1981 | Shimizu et al. | 585/428 |
| 4,308,414 | 12/1981 | Wiegers et al. | 585/525 |
| 4,440,966 | 4/1984 | Ferber et al. | 585/415 |

FOREIGN PATENT DOCUMENTS

| | | | |
|---|---|---|---|
| 2095281 | 9/1982 | United Kingdom | 585/323 |
| 670555 | 2/1978 | U.S.S.R. | 585/426 |

OTHER PUBLICATIONS

Corson et al., J. Org. Chem., 27, 1636–1640, (1962).

Primary Examiner—Andrew H. Metz
Assistant Examiner—A. Pal
Attorney, Agent, or Firm—Stephen E. Reiter

[57] ABSTRACT

The self condensation of monovinyl aromatic compounds to acyclic dimers, the cross-reaction of monovinyl aromatic compounds with olefins in the presence of acid catalysts to produce cyclialkylated aromatic compounds, and the production of cyclialkylated aromatic compounds by reaction of olefins with acyclic dimers of monovinyl aromatic compounds in the presence of acid catalysts is improved by employing a tetrahydrothiophene 1,1-dioxide solvent.

21 Claims, No Drawings

ACID CATALYZED REACTIONS OF MONOVINYL AROMATIC COMPOUNDS

This invention relates to alkylation reactions of monovinyl aromatic compounds in the presence of acid catalysts. In one aspect, the invention relates to the self-condensation of monovinyl aromatic compounds to produce acyclic dimers. In another aspect, the invention relates to the alkylation of monovinyl aromatic compounds with olefinic compounds to produce cyclic alkylated aromatic products.

BACKGROUND OF THE INVENTION

The acid catalyzed dimerization of monovinyl aromatic compounds frequently leads to the predominant production of cyclic dimers, rather than the acyclic dimers desired. The production of acyclic dimers is desirable because acyclic dimers are useful as chemical intermediates for the preparation of a variety of products. When, instead, monovinyl aromatic compounds are subjected to acid conditions in the presence of olefins, cyclic alkylation of the monovinyl aromatic compound can occur and is frequently the desired process. Unfortunately, the propensity of monovinyl aromatic compounds to self-condense and form cyclic dimers leads to low yields of the desired cyclialkylated products.

OBJECTS OF THE INVENTION

It is, therefore, an object of the invention to produce acyclic dimers of monovinyl aromatic compounds while minimizing the formation of cyclic dimers.

Another object of the invention is the production in high yield of cyclialkylated aromatic compounds by the acid catalyzed reaction of monovinyl aromatic compounds with olefins.

Yet another object of the invention is the production of cyclialkylated aromatic compounds by the acid catalyzed reaction of olefins with acyclic dimers of monovinyl aromatic compounds.

These and other objects of the invention will become apparent from the disclosure and claims provided herein.

In accordance with yet another embodiment of the invention, I have discovered that cyclialkylated product can be produced from acylic dimers of monovinyl aromatic compounds by contacting the acyclic dimer, olefin and an acid catalyst in the presence of a tetrahydrothiophene 1,1-dioxide solvent.

STATEMENT OF THE INVENTION

In accordance with the present invention, I have discovered that the yield of acyclic dimer formed in the acid catalyzed reaction of monovinyl aromatic compounds can be greatly increased by carrying out the reaction in the presence of a tetrahydrothiophene 1,1-dioxide solvent.

In accordance with another embodiment of the present invention, I have discovered that the yield of cyclialkylated product formed in the acid catalyzed reaction of monovinyl aromatic compounds with olefins can be greatly increased by carrying out the reaction in the presence of a tetrahydrothiophene 1,1-dioxide solvent.

DETAILED DESCRIPTION OF THE INVENTION

In accordance with the present invention, a process is provided for the dimerization of monovinyl aromatic compounds to produce acyclic dimers which comprises contacting monovinyl aromatic compounds in the presence of an acid catalyst and a tetrahydrothiophene 1,1-dioxide solvent.

In accordance with another embodiment of the present invention, a process is provided for producing cyclialkylated products from monovinyl aromatic compounds and olefinic compounds which comprises contacting the aromatic and olefinic compounds in the presence of an acid catalyst and a tetrahydrothiophene 1,1-dioxide solvent.

In accordance with yet another embodiment of the present invention, a process is provided for the preparation of cyclialkylated products from acyclic dimers of monovinyl aromatic compounds and olefins comprising contacting acyclic dimer and olefin in the presence of an acid catalyst and a tetrahydrothiophene 1,1-dioxide solvent.

Tetrahydrothiophene 1,1-dioxide solvents useful in the practice of the present invention conform to the following formula:

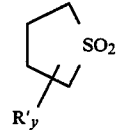

wherein R' is a $C_1$–$C_{10}$ carbon radical, a halide or an alkoxy derivative having the structure —OR, wherein R is H or a $C_1$–$C_{10}$ carbon radical and y is 0–4, inclusive. Examples of suitable solvents are tetrahydrothiophene 1-1-dioxide (sulfolane), 2-methyltetrahydrothiophene 1,1-dioxide, 3-methyl-tetrahydrothiophene 1,1-dioxide, 2-ethyltetrahydrothiophene 1,1-dioxide, 3-ethyltetrahydrothiophene 1,1-dioxide, 2,5-dimethyltetrahydrothiophene 1,1-dioxide and the like, and mixtures of any two or more thereof.

Monovinyl aromatic compounds which are useful in the practice of the present invention conform to one of the following formulae:

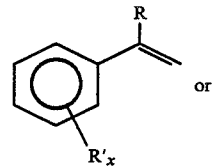

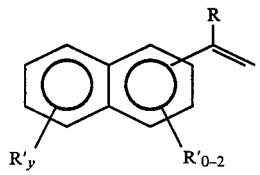

wherein R, R' and y are as defined above and x is 0–4, inclusive, with the proviso that at least one ortho position with respect to the vinyl substituent is not substituted. Examples of monovinyl aromatic compounds which satisfy the above formulae include styrene, alpha-methylstyrene, vinylnaphthalene, 4-methyl-alpha-methylstyrene, and the like. A presently preferred monovinyl aromatic compound is alpha-methylstyrene because of its ready availability, proven reactivity and established utility of the reaction products.

When monovinyl aromatic compounds are allowed to self-react in the presence of acid catalysts, the desired acyclic dimers produced can be represented by the following formulae:

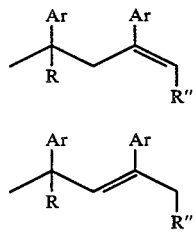

wherein R is H or a $C_1$–$C_{10}$ carbon radical, R" is H or a $C_1$–$C_9$ carbon radical and Ar is an aromatic or substituted aromatic ring having 6–20 carbon atoms.

Acid catalysts suitable for the practice of the present invention include those acidic materials which are functional in aqueous systems and are capable of acting as Friedel-Crafts condensing catalysts. Examples include phosphoric acid, sulfuric acid, trifluoroacetic acid, methanesulfonic acid, and the like. When phosphoric acid is employed as the acid catalyst, it is preferred that an acid concentration of about 92 to 100% be employed. When sulfuric acid is employed as the reaction catalyst, it is preferred that the sulfuric acid concentration be within the range of about 75 to 90%.

In carrying out the process of the invention, the proportions of the ingredients employed may be varied over wide limits. It is preferred to use at least one part monovinyl aromatic compound by volume per part of acid catalyst, up to a volume ratio of about 1000 parts monovinyl aromatic compound per part acid catalyst. Most preferably, the volume ratio of acid catalyst employed will range from about 2 to 50 parts per 100 parts of monovinyl aromatic compound.

In carrying out the process of the present invention, at least one part by volume of tetrahydrothiophene 1,1-dioxide solvent per 100 parts of monovinyl aromatic compound up to about 100 parts by volume of tetrahydrothiophene 1,1-dioxide solvent per 100 parts of monovinyl aromatic compound; preferably, about 2 to 50 parts by volume of the tetrahydrothiophene 1,1-dioxide per 100 parts of monovinyl aromatic compound will be employed.

In accordance with one embodiment of the present invention, the tetrahydrothiophene 1,1-dioxide solvent and acid catalyst are admixed. Thereafter, the monovinyl aromatic compound is added slowly to the solvent containing catalyst. The reaction temperature is maintained at about 0° to 200° C. for about 0.5 to 48 hours. The reaction temperature and time required for a given reaction will vary depending on the catalyst and reagents employed. In addition, at higher reaction temperatures, shorter reaction time is required and vice versa. When reaction is complete, the reaction mixture is quenched, such as for example, with water, or the acid catalyst is separated. After being neutralized, the reaction mixture can be analyzed by gas liquid chromatography or subjected to vacuum distillation for product recovery.

In accordance with another embodiment of the present invention, monovinyl aromatic compounds can be contacted with acid catalysts as hereinabove described and in the further presence of olefinic compounds to produce cyclialkylated aromatic products. It has been found that the yield of the desired cyclialkylated aromatic product is greatly improved when this reaction is carried out in the presence of a tetrahydrothiophene 1,1-dioxide solvent.

Suitable olefinic compounds are broadly contemplated to be organic compounds having at least one carbon-carbon double bond and any substituents which do not detrimentally interact with the catalyst employed for the alkylation reaction. Preferred olefinic compounds employed in the practice of the invention are mono-olefins. Those mono-olefins having 4 up to about 30 carbon atoms with only one carbon-carbon double bond, and which are capable of forming tertiary carbocations under the alkylation process conditions are especially preferred, because the possibility of multiple alkylation reactions with consequent formation of a mixture of products is minimized.

The especially preferred group of olefinic compounds useful in the practice of my invention can also be described by the formula

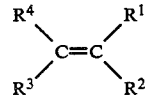

wherein each of $R^1$, $R^2$, $R^3$ and $R^4$ are independently selected from hydrogen and $C_1$ through $C_{10}$ alkyl or cycloalkyl radicals. In addition, $R^1$ and $R^2$ can be joined as part of a polymethylene radical or a halogen-, alkyl- or cycloalkyl-substituted polymethylene radical having about 2 to about 20 carbon atoms, i.e., a carbocyclic compound with an exocyclic double bond. Further, $R^1$ and $R^4$ can be similarly joined as part of a polymethylene radical or a halogen-, alkyl-, or cycloalkyl-substituted polymethylene radical having about 2 to about 20 carbon atoms, i.e., a carbocyclic compound with an endocyclic double bond.

Examples of olefinic compounds useful in the practice of the invention include isobutylene, 2-methyl-1-butene, 2-methyl-2-butene, 2,3-dimethyl-2-butene, neohexene (tertiary-butylethylene), diisobutylene (2,4,4-trimethyl-1-pentene), 2-butene, 2-pentene, 1-methylcyclohexene, 1-methylcyclopentene, 2-hexene, and the like.

The molar ratio of olefinic compound to monovinyl aromatic compound employed in the practice of the invention can vary broadly. In order to provide further guidance, it is suggested that a molar ratio of olefinic compound to monovinyl aromatic compound of at least about 0.05:1 up to about 5:1 be employed. Ratios below the lower value provide low product yield based upon the amount of starting material employed, while ratios above the upper value have a tendency to produce undesirable levels of by-products. Ratios of about 0.2:1 up to about 3:1 are preferred for efficient use of starting materials and minimum formation of by-products, which in turn simplifies the task of product recovery.

In accordance with yet another embodiment of the present invention, it has been found that cyclialkylated aromatic compounds can be prepared by contacting acyclic dimers of monovinyl aromatic compounds having the structure detailed above with olefinic compounds in the presence of acid catalyst and at least one tetrahydrothiophene 1,1-dioxide solvent. Thus, the acyclic dimer of monovinyl aromatic compound can be purposefully made in a separate reaction step, such as for example, via the process described in detail above. Alternatively, the acyclic dimer recovered as by-product from another reaction, such as for example, the cyclialkylation reaction described above, can be employed as the source of the aromatic portion of the cyclialkylated aromatic product in this embodiment of the invention.

A further understanding of the present invention and its advantages will be provided by reference to the following non limiting examples.

EXAMPLE I

Dimerization of Alpha-Methylstyrene in the Absence of Sulfolane

A control dimerization reaction was carried out by adding 50 mL of α-methylstyrene to 20 mL of 85% phosphoric acid over about 20 minutes. The addition was performed with thorough stirring, and vessel temperature increased from about 25° C. to about 46° during the addition. When addition of α-methylstyrene was complete, vessel temperature was maintained at 45°–55° C. for 8 hours.

At various reaction times, samples were withdrawn, washed with water, then analyzed by gas liquid chromatography (glc). Reaction results are summarized below.

TABLE I

| Reaction Time, hrs. | α-Methylstyrene Conversion, % | Product Selectivity*, % | | |
|---|---|---|---|---|
| | | D-1 | D-2 | TMI |
| 4 | 75 | 56 | — | 34 |
| 8 | 97 | 54 | 6 | 34 |

*D-1 = acyclic dimer 1 = 2,4-diphenyl-4-methyl-1-pentene
D-2 = acyclic dimer 2 = 2,4-diphenyl-4-methyl-2-pentene
TMI = 1,1,3-trimethyl-3-phenylindane

EXAMPLE II

Dimerization of Alpha-Methylstyrene in the Presence of Sulfolane

Invention dimerization reactions were carried out according to the procedure set forth in Example I, further employing 20 mL of sulfolane admixed with the phosphoric acid. Reaction results are summarized in Table II.

TABLE II

| Reaction Time, hrs. | α-Methylstyrene Conversion, % | Product Selectivity*, % | | |
|---|---|---|---|---|
| | | D-1 | D-2 | TMI |
| 4 | 98 | 92 | 5 | <1 |
| 8 | 98 | 89 | 7 | <1 |

*D-1 = acyclic dimer 1 = 2,4-diphenyl-4-methyl-1-pentene
D-2 = acyclic dimer 2 = 2,4-diphenyl-4-methyl-2-pentene
TMI = 1,1,3-trimethyl-3-phenylindane Comparison of the results presented in Tables I and II demonstrates that the conversion of α-methylstyrene and the selectivity to the acyclic dimer, 2,4-diphenyl-4-methyl-1-pentene, are significantly improved when reaction is carried out in the presence of a tetrahydrothiophene 1,1-dioxide such as sulfolane.

EXAMPLE III

Preparation of 1,1,2,3,3-Pentamethylindane from Alpha-Methylstyrene and 2-Methyl-2-butene Fifty milliliters of a 1:1 molar ratio mixture of alpha-methylstyrene and 2-methyl-2-butene (27.5 mL of alpha-methylstyrene and 22.5 mL of 2-methyl-2-butene) was added over about 40 minutes to about 30 mL of 75% sulfuric acid. Once reagent addition was complete, stirring was continued for several hours while the temperature was maintained between about 24° to 28° C. To analyze the reaction, a sample was withdrawn, washed with water and analyzed by glc. Reaction results are summarized in Table III designated as run 1.

The same procedure employed in the previous paragraph was repeated, further employing 20 mL of sulfolane mixed with the 30 mL of aqueous sulfuric acid. Reaction results are summarized in Table III, designated as run 2.

A third run was carried out by adding 50 mL of a 1:1 molar ratio of alpha-methylstyrene and 2-methyl-2-butene to a mixture of 20 mL of 85% phosphoric acid and about 15 g of $P_2O_5$ (the mixture producing approximately 100% phosphoric acid). The reaction employing phosphoric acid catalyst was carried out at a temperature in the range of about 49°–52° C. Reaction results are summarized in Table III, designated as run 3.

The same procedure as employed in the previous paragraph was repeated, further employing about 20 mL of sulfolane admixed with the 100% phosphoric acid. Reaction results are summarized in Table III, designated as run 4.

Yet another run was carried out with phosphoric acid catalyst and added sulfolane. This time, 20 mL of 85% phosphoric acid and 20 mL of sulfolane were admixed, then the 1:1 molar ratio mixture of alpha-methylstyrene was added as described above. Reaction results are summarized in Table III, designated as run 5.

TABLE III

| Run | Acid, conc. % | Sulfolane Added | α-Methylstyrene Conversion, % | Product Selectivity,* % | |
|---|---|---|---|---|---|
| | | | | PMI | TMI |
| 1 | Sulfuric, 75 | No | >90 | 49 | 24 |
| 2 | Sulfuric, 75 | Yes | 90 | 63 | 18 |
| 3 | Phosphoric, 100 | No | 100 | 37 | 37 |
| 4 | Phosphoric, 100 | Yes | 100 | 54 | 13 |
| 5 | Phosphoric, 85 | Yes | 100 | 4 | 92** |

*PMI = 1,1,2,3,3-pentamethylindane
TMI = 1,1,3-Trimethyl-3-phenylindane
**Mixed dimers =
81% D-1 (2,4-diphenyl-4-methyl-1-pentene),
10% D-2 (2,4-diphenyl-4-methyl-2-pentene), and
1% TMI (1,1,3-trimethyl-3-phenylindane)

The results presented in Table III demonstrate the improved selectivity to cyclialkylated product obtained when reaction is carried out in the presence of a tetrahydrothiophene dioxide such as sulfolane, compare runs 1 and 2; 3 and 4. Run 5 demonstrates that 85% phosphric acid is not a sufficiently strong acid to promote cyclialkylation of alpha-methylstyrene with 2-methyl-2-butene under the conditions employed.

EXAMPLE IV

Cyclialkylation of an Acyclic Dimer of α-Methylstyrene with 2-Methyl-2-butene

While the temperature of a mixture of 15 mL of 75% aqueous sulfuric acid and 10 mL of sulfolane was maintained at about 33° to 38° C., a mixture comprising 8.5 mL of 2,4-diphenyl-4-methyl-1-pentene (an acyclic dimer of α-methylstyrene, see Example I) and 9.5 mL of 2-methyl-2-butene was added with stirring over about 10 minutes. Stirring at the same temperature was maintained for a total of 4 hours. Periodic samples were withdrawn and analyzed by washing with water, then subjecting to glc analysis. Results at different reaction times are summarized in Table IV.

TABLE IV

| Reaction Time, hr. | D-1* Conversion, % | GLC Analysis, %** | | | |
|---|---|---|---|---|---|
| | | PMI | D-1 | D-2 | D-3 |
| 1 | 95 | 45 | 5 | 19 | 12 |
| 4 | 98 | 51 | 2 | 6 | 20 |

*D-1 = acyclic dimer of alpha-methylstyrene = 2,4-diphenyl-4 methyl-1-pentene
**PMI = 1,1,2,3,3-pentamethylindane
D-2 = acyclic dimer of alpha-methylstyrene = 2,4-diphenyl-4-methyl-2-pentene
D-3 = cyclic dimer of alpha-methylstyrene = 1,1,3-trimethyl-3-phenylindane The results of these experiments demonstrate that acyclic dimers of α-methylstyrene can be employed as the starting material for the preparation in good yield of cyclialkylated products of α-methylstyrene.

EXAMPLE V

A mixture of about 10 mL of 2,4-diphenyl-4-methyl-2-pentene (acyclic dimer of alpha-methylstyrene, referred to as D-2) and 10 mL of 2-methyl-2-butene was added over a period of about 15 minutes to a stirred mixture of 10 mL of sulfolane and 15 mL of 75% sulfuric acid, maintained at about 34° C. Once addition was complete, the mixture was stirred for about 4 hours, before reaction was quenched by a water wash, then analyzed by glc. Results are summarized in Table V.

TABLE V

| Run | Aromatic Reactant* | Product Selectivity,** % | | | |
|---|---|---|---|---|---|
| | | PMI | D-1 | D-2 | D-3 |
| 6 | α-MS | 55 | 1 | 3 | 22 |
| 7 | D-1 | 51 | 2 | 6 | 20 |
| 8 | D-2 | 44 | 4 | 14 | 20 |
| 9 | D-1/D-2/D-3*** | 40 | ND | 4 | 41 |

*Aromatic reactant:
α-MS = alpha-methylstyrene
D-1 = 2,4-diphenyl-4-methyl-1-pentene
D-2 = 2,4-diphenyl-4-methyl-2-pentene
D-3 = 1,1,3-trimethyl-3-phenylindane
**Products
PMI = 1,1,2,3,3-pentamethylindane
D-1, D-2, D-3, see above.
***Charge ratio of the mixture was 34%/20%/43%
ND = not detectable.

Run 6 is a comparison run showing the yield of 1,1,2,3,3-pentamethylindane (PMI) obtained directly from α-methylstyrene and 2-methyl-2-butene. Runs 7, 8 and 9 demonstrate that good yields of PMI are also obtained when acyclic dimers of alpha-methylstyrene, D-1 and D-2, as well as mixtures thereof, are used as the aromatic moiety to be alkylated. The results of runs 7, 8 and 9 suggest that the order of reactivity of the various alpha-methylstyrene dimers is D-1>D-2>D-3.

The examples have been provided merely to illustrate the practice of my invention and should not be read so as to limit the scope of my invention or the appended claims in any way. Reasonable variations and modifications not departing from the essence and spirit of my invention, are contemplated to be within the scope of patent protection desired and sought.

I claim:

1. A process for preparing acyclic dimers of monovinyl aromatic compounds having the formula

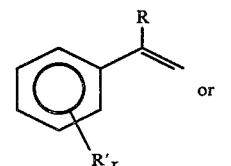 or

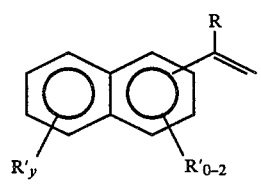

wherein R is H or a $C_1$–$C_{10}$ carbon radical, R' is a $C_1$–$C_{10}$ carbon radical, a halide or an alkoxy derivative having the structure —OR, wherein R is as defined above, x is 0–4, inclusive, with the proviso that at least one ortho position with respect to the vinyl substituent is not substituted, and y is 0–4, inclusive, said process comprising
   contacting said monovinyl aromatic compound in the presence of an acid catalyst and at least one tetrahydrothiophene 1,1-dioxide having the formula:

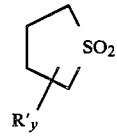

wherein each R' is independently as defined above and y is as defined above, under conditions suitable for the formation of acyclic dimers.

2. A process in accordance with claim 1 wherein said acid catalyst is at least one selected from the group consisting of:
   $H_3PO_4$, and
   $H_2SO_4$.

3. A process in accordance with claim 1 wherein the volume/volume ratio of said monovinyl aromatic compound to said acid catalyst is within the range of 1 to 1000:1.

4. A process in accordance with claim 1 wherein the volume/volume ratio of said monovinyl aromatic compound to said tetrahydrothiophene 1,1-dioxide is within the range of 1 to 100:1.

5. A process in accordance with claim 1 wherein said tetrahydrothiophene 1,1-dioxide is sulfolane.

6. A process in accordance with claim 1 wherein said monovinyl aromatic compound is alpha-methylstyrene.

7. A process for preparing cyclialkylated aromatic compounds which comprises contacting the product of claim 1 with at least one olefinic compound having the formula

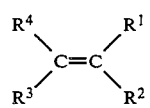

wherein each of $R^1$-$R^4$ is independently selected from H and $C_1$-$C_{10}$ alkyl or cycloalkyl radical; or $R^1$ and $R^2$ or $R^1$ and $R^4$ can be joined as part of a polymethylene or alkyl- or cycloalkyl-substituted polymethylene radical having two to about 20 carbon atoms, wherein said olefinic compound is capable of forming a tertiary carbocation under the process conditions, in the presence of:

(i) an acid catalyst and
(ii) at least one tetrahydrothiophene 1,1-dioxide having the formula:

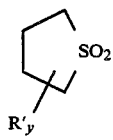

wherein each R' is independently a $C_1$-$C_{10}$ carbon radical, a halide, or an alkoxy derivative having the structure —OR, wherein R is H or a $C_1$-$C_{10}$ carbon radical, and y is 0–4, inclusive, under conditions suitable for the formation of cyclialkylated aromatic product.

8. A process in accordance with claim 7 wherein said olefinic compound is selected from the group consisting of:
2-methyl-1-butene,
2-methyl-2-butene,
2,3-dimethyl-1-butene,
3-methyl-1-butene,
neohexene,
isobutylene, and
diisobutylene.

9. A process for preparing cyclialylated products from monovinyl aromatic compounds and olefinic compounds which comprises contacting
(a) at least one aromatic compound having the formula

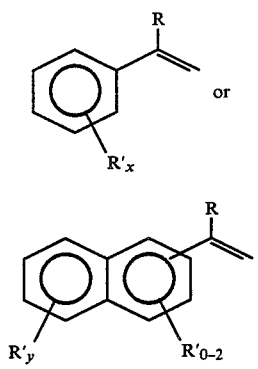

wherein R is H or a $C_1$-$C_{10}$ carbon radical, R' is a $C_1$-$C_{10}$ carbon radical, a halide or an alkoxy derivative having the structure —OR, wherein R is as defined above, x is 0–4, inclusive, with the proviso that at least one ortho position with respect to the vinyl substituent is not substituted, and y is 0–4, inclusive, and
(b) at least one olefinic compound having the formula:

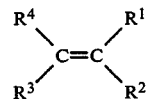

wherein each of $R^1$-$R^4$ is independently selected from H and $C_1$-$C_{10}$ alkyl or cycloalkyl radical; or $R^1$ and $R^2$ $^{1\,or\,R2}$ or $R^1$ and $R^4$ can be joined as part of a polymethylene or alkyl- or cycloalkyl-substituted polymethylene radical having two to about 20 carbon atoms, wherein said olefinic compound has 4 up to 30 carbon atoms, and wherein said olefinic compound is capable of forming a tertiary carbocation under the process conditions, in the presence of
(i) an acid catalyst and
(ii) at least one tetrahydrothiophene 1,1-dioxide having the formula:

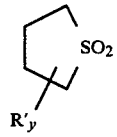

wherein each R' is independently as defined above and y is as defind above, under conditions suitable for the formation of cyclialkylated aromatic product.

10. A process in accordance with claim 9 wherein said acid catalyst is at least one selected from the group consisting of:
$H_3PO_4$, and
$H_2SO_4$.

11. A process in accordance with claim 9 wherein the volume/volume ratio of said monovinyl aromatic compound to said acid catalyst is within the range of 1 to 1000:1.

12. A process in accordance with claim 9 wherein the volume/volume ratio of said monovinyl aromatic compound to said tetrahydrothiophene dioxide is within the range of 1 to 100:1.

13. A process in accordance with claim 9 wherein said tetrahyrothiophene 1,1-dioxide is sulfolane.

14. A process in accordance with claim 9 wherein said monovinyl aromatic compound is alpha-methylstyrene.

15. A process in accordance with claim 9 wherein said olefinic compound is selected from the group consisting of:
2-methyl-1-butene,
2-methyl-2-butene,
2,3-dimethyl-1-butene,
3-methyl-1-butene,
neohexene,
isobutylene, and
diisobutylene.

16. A process for preparing cyclialkylated products which comprises contacting
(a) at least one acyclic dimer of a monovinyl aromatic compound having the formula:

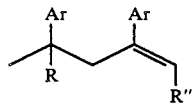

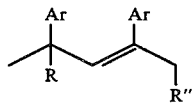

wherein R is H or a $C_1$–$C_{10}$ carbon radical, R″ is H or a $C_1$–$C_9$ carbon radical and Ar is an aromatic or substituted aromatic ring having 6–20 carbon atoms, and (b) at least one olefinic compound having the formula:

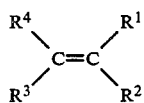

wherein each of $R^1$–$R^4$ is independently selected from H and $C_1$–$C_{10}$ alkyl or cycloalkyl radical; or $R^1$ and $R^2$ or $R^1$ and $R^4$ can be joined as part of a polymethylene or alkyl- or cycloalkyl-substituted polymethylene radical having two to about 20 carbon atoms, wherein said olefinic compound has 4 up to 30 carbon atoms, and wherein said olefinic compound is capable of forming a tertiary carbocation under the process conditions, in the presence of (i) an acid catalyst and (ii) at least one tetrahyrothiophene 1,1-dioxide having the formula:

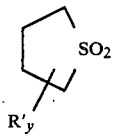

wherein each R′ is independently a $C_1$–$C_{10}$ carbon radical, a halide or an alkoxy derivative having the structure —OR, wherein R is H or a $C_1$–$C_{10}$ carbon radical and y is 0–4, inclusive, under conditions suitable for the formation of cyclialkylated aromatic product.

17. A process in accordance with claim 16 wherein said acid catalyst is at least one selected from the group consisting of:
$H_3PO_4$, and
$H_2SO_4$.

18. A process in accordance with claim 16 wherein the volume/volume ratio of said monovinyl aromatic compound to said acid catalyst is within the range of 1 to 1000:1.

19. A process in accordance with claim 16 wherein the volume/volume ratio of said monovinyl aromatic compound to said tetrahydrothiophene 1,1-dioxide is within the range of 1 to 100:1.

20. A process in accordance with claim 16 wherein said tetrahydrothiophene 1,1-dioxide is sulfolane.

21. A process in accordance with claim 16 wherein said olefinic compound is selected from the group consisting of:
2-methyl-1-butene,
2-methyl-2-butene,
2,3-dimethyl-1-butene,
3-methyl-1-butene,
neohexene,
isobutylene, and
diisobutylene.

* * * * *

UNITED STATES PATENT AND TRADEMARK OFFICE
CERTIFICATE OF CORRECTION

PATENT NO. : 4,596,896
DATED : 6/24/86
INVENTOR(S) : Raymond L. Cobb

It is certified that error appears in the above-identified patent and that said Letters Patent is hereby corrected as shown below:

Col. 9, Claim 9, line 38 "cyclialylated" should be --cyclialkylated--

Col. 10, Claim 9, line 10 "$R^1_4$ and $R^2$ 1 or $R^2$ or $R^1$ and $R^4$" should be --$R^1$ and $R^2$ or $R^1$ and $R^4$--

Col. 10, Claim 13, line 49 "tetrahyrothiophene" should be --tetrahydrothiophene--

Col. 11, Claim 16, line 39 "tetrahyrothiophene" should be --tetrahydrothiophene--

Signed and Sealed this

Twenty-third Day of September 1986

[SEAL]

Attest:

DONALD J. QUIGG

Attesting Officer

Commissioner of Patents and Trademarks